United States Patent [19]

Rizkalla

[11] Patent Number: 4,792,420

[45] Date of Patent: Dec. 20, 1988

[54] PURIFICATION OF CARBOXYLIC ACID ANHYDRIDES

[75] Inventor: Nabil Rizkalla, River Vale, N.J.

[73] Assignee: Eastman Kodak Company, Rochester, N.Y.

[21] Appl. No.: 758,632

[22] Filed: Jul. 24, 1985

[51] Int. Cl.$^4$ ............................................. C07C 51/573
[52] U.S. Cl. ................................ 260/546; 260/544 A; 260/549
[58] Field of Search .................... 260/546, 549, 544 A

[56] References Cited

U.S. PATENT DOCUMENTS 4,255,591  3/1981  Makin et al. ........................ 260/546
4,335,059  6/1982  Rizkalla ............................... 260/549

FOREIGN PATENT DOCUMENTS 0143179  6/1985  European Pat. Off. .
3331548  3/1985  Fed. Rep. of Germany .

Primary Examiner—Werren B. Lone

[57] ABSTRACT

Carboxylic acid anhydrides are freed from small amounts of halogen and halide moieties by treatment with hydrogen and carbon monoxide in the presence of a supported Group VIII noble metal catalyst.

2 Claims, No Drawings

PURIFICATION OF CARBOXYLIC ACID ANHYDRIDES

This invention relates to the purification of carbonylation products and is more particularly concerned with the purification of carboxylic acid anhydrides, especially acetic anhydride.

Processes have been developed for the preparation of carboxylic acid anhydrides by the reaction of olefins, esters, and ethers with carbon monoxide in the presence of a catalyst system which comprises a metal catalyst component and an iodide component, generally an alkyl iodide, especially methyl iodide. Processes of this character involving a Group VIII noble metal catalyst, such as rhodium, palladium, iridium and the like are disclosed, for example, in U.S. Pats. Nos. 3,852,346, 4,115,444, 4,335,059, and 4,358,411, and in British Pats. Nos. 1,468,940 and 1,523,346. Catalyst systems of the character indicated wherein the metal component comprises nickel or nickel compounds are employed for the preparation of carboxylic anhydrides in processes which are disclosed, for example, in U.S. Pats. Nos. 4,026,677 and 4,026,678. Processes have also been disclosed wherein carboxlyic anhydrides are co-produced with carboxylic acids in carbonylation systems involving Group VIII noble metal catalysts and an iodide promoter. In European patent applications 0 087 869 and 0 087 870, for example, there are described processes involving the carbonylation of carboxylic acid esters, such as methyl acetate, hydrocarbyl ethers, such as dimethyl ether, and optionally also an alcohol, together with controlled, limited amounts of water. Similarly, U.S. Pat. No. 4,046,807 shows the preparation of acetic anhydride by the carbonylation of methyl acetate with a Group VIII noble metal catalyst and an iodide, wherein methanol is mixed with the methyl acetate feedstock and is converted to acetic acid so that acetic anhydride and acetic acid are co-produced in the same reaction zone. Carbonylation processes for the preparation of carboxylic acid anhydrides have also been disclosed in which the carbonylation of carboxylic acid esters and/or hydrocarbyl ethers is carried out with various catalysts, such as catalysts based on metals of Group VIII of the Periodic Table, in the presence of an iodide and in the presence of substantial quantities of carboxylic acids, especially acetic acid. Processes of this nature are disclosed, for example, in U.S. Pats. Nos. 4,115,444, 4,333,884 and 4,333,885. In the reductive carbonylation of methyl acetate or dimethyl ether to produce ethylidene diacetate as described, for example, in British Pat. No. 1,538,782, quantities of acetic anhydride are co-produced. The effluents from the processes such as referred to above are treated, usually by distillation, to separate the relatively non-volatile metal-containing catalyst component, and the liquid effluent is then separated, as by fractional distillation, into its several components including the carboxylic acid anhydride present. Whereas the major portion of the halogen or halide moiety in the effluent can be separated by such distillation and recycled to the carbonylation zone to provide the halogen or halide moiety required in the production of further quantities of carbonylation products of the character referred to above, even with relatively efficient distillation, however, the carboxylic acid anhydride recovered inevitably contains a small amount of halogen or a halogen compound, such as methyl iodide.

While the amount of the halogen or halide moiety remaining with the carboxylic acid anhydride is generally very small, yet the carboxylic acid anhydride is contaminated to an extent that is undesirable in many cases and frequently interferes with its utilization. Attempts to eliminate or reduce the quantity of the halogen or halide contaminant to acceptable levels by fractional distillation have presented problems. One of the problems encountered results from the fact that carbonylation products contain species of halogen contaminants that are highly resistant to separation by distillation. U.S. Pat. No. 4,246,195 provides a process for removing iodine moieties, especially organic iodine compounds, from carbonylation products by treating the iodine-contaminated products with cesium acetate, potassium acetate, or sodium acetate. The removal of iodine contaminants from carboxylic acids has been proposed in various patents. Thus, U.S. Pat. No. 3,772,156 purifies acetic acid to remove iodine by multiple distillation combined with treatment with one or more chemical agents. U.S. Pat. No. 3,709,795 treats the carboxylic acid with an inorganic oxidizing compound and then subjecting the treated carboxylic acid to distillation. U.S. application of H. M. Sachs and M. Becker Ser. No. 335,918 suggests the removal of iodine contaminants from acetic acid and acetic anhydride by use of an anion exchange resin. While these several processes are effective to various degrees, it is desirable to provide a less complicated method of treatment which, at the same time, is capable of reducing the halogen or halide contaminant to very low levels.

It is accordingly an object of this invention to provide an improved process for the removal of halogen or halide contaminants from carboxylic acid anydrides recovered from carbonylation and like reaction mixtures which is effective to reduce such contaminants to low levels.

In accordance with the invention, it has been surprisingly discovered that when the reaction component to be purified is treated with hydrogen in the presence of a supported catalyst under moderate temperature and pressure conditions and for a relatively short time, the halide or halogen moieties present as contaminants in the carboxylic acid anhydride and normally resistant to separation by distillation can be substantially completely removed to leave an effluent which is essentially free from the halide or halogen moieties, i.e., they remain in concentrations of only a few parts per billion (ppb) and in a wholly-acceptable form for commercial use.

Thus, in accordance with the process of this invention, a liquid or vaporous body of the carboxylic acid anhydride to be purified, and which is contaminanted with a small amount of halide or halogen moieties, is intimately contacted with a supported catalyst while a gaseous stream comprising hydrogen flows into the carboxylic acid anhydride being treated. It has been surprisingly discovered that such treatment "strips" and removes the halogen or halide moieties from the carboxylic acid anhydride-containing body with the result that when the stream leaves the contact zone containing the catalyst, it is essentially free of halogen or halide moieties of any kind and is of a high purity with respect to its content of halogen values.

The carbonylation reaction component fed to the process of this invention consists essentially of a carboxylic acid anhydride, or a mixture of carboxylic acid anhydrides, e.g., acetic anhydride, propionic anhydride, n-butyric anhydride, hexanoic anhydride and other carboxylic acid anhydrides containing up to 8 carbon atoms, and contains halogen or halide impurities corresponding to or derived from the halogen or halide moieties present in the reaction zone wherein the carboxylic acid anhydride is present in the carbonylation reaction mixture produced by the carbonylation of olefins, esters or ethers in the presence of a Group VIII metal-containing catalyst and a halogen moiety, such as described in the above-mentioned U.S. Pats. Nos. 3,852,346, 4,026,678, 4,115,444, 4,335, 059 and 4,358,411, and in British Pats. No. 1,468,940 and 1,523,346. The disclosures of said U.S. and British patents are incorporated herein by reference. The process of this invention is carried out in a substantially water-free system. The carboxylic acid anhydride stream to be treated will ordinarily be essentially free of other componets in addition to the halogen or halide contaminants, but the stream may contain carbonylation-derived components such as carboxylic acids, esters, ethers, ethylidene diacetate, alcohols, and the like. Ordinarily, it is preferred that the total of such other components not exceed about 25 wt. % of the carboxylic acid anhydride stream.

The halogen and halide impurity contect of the carboxylic acid anhydride feed to the process of the invention can vary, the limiting factor on the impurity level in the feed being essentially an economic one. Extensive removal of impurities from the feed by distillation prior to application of the process of this invention is generally uneconomic and, practically speaking, has not been found to be feasible. However, the greater the content of halogen and halide impurity in the feed to the process of this invention, the more extensive the treatment required. In each case, therefore, the impurity level in the feed involves an economic balance between cost of prior distillation and use of the treatment of this invention. Such considerations normally dictate feeds containing under 1,000 ppm of halogen and halide impurities, generally less than 500 ppm, and usually at most 300 ppm, all amounts referring to contained halogen, based on total feed. At least 0.001 ppm is ordinarily present.

The catalysts used in the process of the invention are insoluble in the body of carboxylic acid anhydride being insoluable in the body of carboxylic acid anhydride being treated and are thus heterogeneous catalysts as distinguished from soluble or homogeneous catalysts. The catalysts include the noble metals of Group VIII of the Periodic Table, such as palladium, platinum, osmium, ruthenium, and the like. The metal catalysts are, as mentioned, supplied and used in supported form, i.e., carried on or dispersed on a support or carrier which is of such size that it can be employed in a reactor, e.g., from 400 mesh/inch to ½-inch particle sizes. The range of variation of the pore volume relative to solid weight is from 0.03 to 2.5 cm3/gram of the porous phase, with a preferred range of from 0.05 to 1.5 cm$^3$/gram.

Conventional carrier materials can be used, as exemplified by pumice, alumina, silica, silica-alumina, aged or deactivated silica-alumina cracking catalyst, magnesia, diatomaceous earth, bauxite, titania, zirconia, clays, both natural and acid-treated such as Super-Filtrols, attapulgus clay (attapulgite), lime, magnesium silicate, silicon carbide, activated and unactivated carbons, zeolites as well as the zeolitic molecular sieves, solid foams, such as ceramic honeycombs, and porous organic polymers. The above carriers are used as regular and irregular particles and as capilary tubes, and interspacing elements such as shapes, extrudates, ceramic rods, balls, broken pieces, titles, and the like, disposed within the reactor. Activated carbon is the preferred carrier.

The catalyst component can be applied to the carrier in conventional manner, e.g., by impregnation of the carrier with a solution of a soluble compound of the catalyst metal, e.g., palladium, such as a halide, nitrate or the like, followed by drying. If desired, the catalyst can be pre-activated, for example, by heating it in the presence of hydrogen. Catalyst component concentration upon the carrier may vary widely, e.g., 0.01-10 wt. %, or higher.

The hydrogen is employed in admixture with 5-80% of carbon monoxide, i.e., 95 hydrogen and 5 carbon dioxide to 20 hydrogen and 80 carbon dioxide by volume, and may also include inert diluents such a nitrogen, methane, and noble gases, if desired. The presence of inert diluents does not affect the reaction, but their presence makes it necessary to increase the rate of gas supplied. The hydrogen should also be essentially dry, i.e., the hydrogen and any diluents should be reasonably free from water. The presence of minor amounts of water such as may be found in the commercial forms of the gases is, however, entirely acceptable.

It is known in the art to hydrogenate acetic anhydride in the liquid phase to produce ethylidene diacetate and/or acetaldehyde. Proceses of this type are disclosed, for example in Fenton U.S. Pat. No. 3,579,566, Wakamatsu et al U. S. Pat. No. 3,631,188, Suzuki U.S. Pat. No. 4,221,918, European patent application 0 034 062, and British Pat. No. 2,075,508. In these proceses, however, it is necessary to use Group VIII noble metals containing or combined with biphyllic ligands or to use a special solvent or to have present a strong acid, such as sulfuric acid, or to add substantial quantities of halogen moieties and, in general, for the desired results, to employ elevated temperatures and pressures. In contrast, the process of the present invention, which is not directed to producing ethylidene diacetate or acetaldehyde from the anhydride being treated but to remove contaminating halogen values, biphyllic ligands are not employed nor are strong acids nor are solvents, and clearly there is no addition of halogen values. A new and unexpected result is accordingly obtained.

Contacting of the carboxylic acid anhydride stream with hydrogen and the supported catalyst can be effected in any convenient manner. For example, contacting may ge effected in a stirred vessel wherein the catalyst particles are slurried with the liquid body with good agitation while the hydrogen-containing gaseous stream is bubbled through the liquid body and the liquid is then recovered by decantation, filtration, centrifuging, distillation, and the like. However, treatment of the carboxylic acid anhydride stream preferably and most advantageously is effected by passing it through a fixed-bed column of the catalyst. Most preferably, the contacting is effected by passing the carboxylic acid anhydride stream containing the undesirable halogen and halide contaminants downwardly through a bed of the catalyst while passing the hydrogen-containing gaseous stream upwardly through the bed in counter-current contact with the carbboxylic acid anhydride stream. As a result of the contact is the presence of the catalyst, the halogen and halide values in the stream fed to the hydrogenation zone, and which are resistant to removal by distillation, are readily carried away by the flowing gaseous stream, and there is recovered a carboxylic acid anhydride stream essentially free of halogen and halide values. The treatment of the invention can be carried out as a batch, semi-continuous or continuous operation, either with manual or automatic control, employing methods and techniques well known in the art.

When the treatment with the catalyst has been carried out by contacting in a stirred vessel containing the catalyst particles slurried in the carboxylic acid anhydride stream, it will, of course, be necessary to filter the treated stream to remove the catalyst for reuse. When the carboxylic acid stream is passed continuously or intermittently through a bed of the catalyst no such filtration is necessary. The treated product may be subjected to a final distillation to recover the desired product in as pure a form as possible. No subsequent distillation may be needed, although a final distillation can be applied if desired to remove any non-halogen-containing contaminants, if present. Such distillations are, of course, known to persons skilled in the art and are not features of the present invention.

The temperatures of the hydrogen stream and of the carboxylic acid anhydride being treated are selected in the case of liquid-phase reaction to keep the acid anhydride in the liquid phase as it is contacted with the catalyst in the reactor and in the vapor phase in the case of vapor-phase reaction at the total pressure and total gas flow rates employed. Ordinarily, the temperature will lie within the range of 20° and 200° C. Higher temperatures can be employed but there is no particular advantage in their use. The rate of flow of the carboxylic acid anhydride stream through the catalyst bed is subject to wide variation but will generally fall in the range of 0.1 to 4 LHSV.

As mentioned, it is a surprising feature of the invention that the liquid leaving the reactor is essentially free of detectable halogen values.

The reaction is carried out in a vacuum or under atmospheric or superatmospheric pressure, but excessively high pressures, which require special high-pressure equipment, are not necessary. In general, the reaction is effectively carried out by employing a pressure which is preferably 50 mmHg to 1,000 psig although a pressure within a broader range can also be employed. Typically, from about atmospheric up to about 50 psig are used. The reaction can be advantageously carried out in a conventional autoclave or fixed-bed reactor.

One of the advantageous features of the invention as applied to a halogen or halide contaminated carboxylic acid anhydride stream derived from a reaction involving carbon monoxide and/or hydrogen in the presence of a halogen moiety is that the gaseous non-carboxylic acid anhydride effluent of the purification of this invention can be fed to the reaction from which the carboxylic acid anhydride is derived to provide some or all of the gaseous feed to that reaction.

The following examples will serve to provide a fuller understanding of the invention, but it is to be understood that they are given for illustrative purposes only and are not to be construed as limitative of the invention. In the examples, which are carried out at atmospheric pressure, all parts and percentages are on a weight basis unless otherwise indicated and the "parts" or "part" mean grams or gram. In the examples "ppm" stands for parts per million and "ppb" stands for parts per billion and analyses were carried out by high pressure liquid chromatography, neutron activation, and polaragraphic analysis. In all cases, hydrogen diluted with carbon monoxide within the range specified above is employed. In the examples, a mixture of 25 % hydrogen and 75% carbon monoxide by volume is used.

EXAMPLE 1

A reaction vessel provided with a refluxing condenser and a magnetic stirrer is charged with 100 parts acetic anhydride containing 0.8 ppm iodine and 1 part 0.3% palladium on silica. The mixture is stirred for two hours at refluxing temperature while a stream of hydrogen is allowed to bubble through the mixture at the rate of 10 liters per hour. Analysis of the liquid reaction effluent indicates the presence of no free iodine or iodine-containing compounds.

EXAMPLE 2

A reaction vessel provided with a refluxing condenser and a magnetic stirrer is charged with 100 parts acetic anhydride containing 0.8 ppm iodine and 1 part 1% palladium on carbon. The mixture is stirred for two hours at refluxing temperature while a stream of hydrogen is allowed to bubble through the mixture at the rate of 10 liters per hour. Analysis of the liquid reaction effluent indicates the presence of no free iodine or iodine-containing compounds.

EXAMPLE 3

A reaction vessel provided with a refluxing condenser and a magnetic stirrer is charged with 100 parts acetic anhydride containing 0.8 ppm iodine and 1 part 0.5% rhodium on alumina. The mixture is stirred for one hour at refluxing temperature while a stream of hydrogen is allowed to bubble through the mixture at the rate of 10 liters per hour. Analysis of the liquid reaction effluent indicates the presence of 79 ppb of iodine or iodine-containin compounds.

EXAMPLE 4

A reaction vessel provided with a refluxng condenser and a magnetic stirrer is charged with 100 parts acetic anhydride containing 0.8 ppm iodine and 1 part 0.5% ruthenium on alumina. The mixture is stirred for one hour at refluxing temperature while a stream of hydrogen is allowed to bubble through the mixture at the rate of 10 liters per hour. Analysis of the liquid rection effluent indicates the presence of no free iodine or iodine-containing componds.

The gaseous stream is ordinarily introduced at the rate of 5–25 mols, e.g., 10, per hour per mol of halogen being removed.

I claim:

1. A process for the purification of carboxylic acid anhydride contaminated with halogen and halide values to reduce the quantity of said values in said carboxylic acid anhydrides, which comprises treating said carboxylic acid anhydrides with a gaseous stream comprising hydrogen and carbon monoxide, said hydrogen being in admixture with 5–80% of carbon monoxide, in the presence of an insoluble Group VIII noble metal catalyst in supported form and thereafter separating said gaseous stream from the treated carboxylilc acid anhydrides and feeding said separated gaseous stream to the reaction from which said contaminated carboxylic acid anhydrides have been derived.

2. A process as defined in claim 1, wherein the carboxylic acid anhydride contains at least 0.001 but at most 1,000 ppm of iodine values expressed as I.

* * * * *